United States Patent [19]
Veronesi

[11] Patent Number: 5,814,338
[45] Date of Patent: Sep. 29, 1998

[54] DRUG DELIVERY SYSTEM

[75] Inventor: Paolo Alberto Veronesi, Milan, Italy

[73] Assignee: Therapicon S.R.L., Milan, Italy

[21] Appl. No.: 765,952

[22] PCT Filed: Jun. 24, 1995

[86] PCT No.: PCT/EP95/02488

§ 371 Date: Jan. 9, 1997

§ 102(e) Date: Jan. 9, 1997

[87] PCT Pub. No.: WO96/01612

PCT Pub. Date: Jan. 25, 1996

[30] Foreign Application Priority Data

Jul. 11, 1994 [GB] United Kingdom ............... 9413951

[51] Int. Cl.⁶ .................................................. A61K 9/48
[52] U.S. Cl. ..................... 424/472; 424/451; 424/456; 424/463; 424/488
[58] Field of Search ..................... 424/472, 451, 424/456, 463, 488

[56] References Cited

U.S. PATENT DOCUMENTS

| | | | |
|---|---|---|---|
| 3,432,594 | 3/1969 | Bauer | 424/33 |
| 3,656,997 | 4/1972 | Cordes | 424/20 |
| 3,959,540 | 5/1976 | Leiberich et al. | 428/35 |
| 4,690,823 | 9/1987 | Lohner et al. | 424/456 |
| 4,816,259 | 3/1989 | Matthews et al. | 424/463 |
| 5,173,304 | 12/1992 | Löhner et al. | 424/456 |
| 5,232,704 | 8/1993 | Franz et al. | 424/456 |

FOREIGN PATENT DOCUMENTS 1232963 9/1989 Japan.

OTHER PUBLICATIONS

J. P. Stanley, Part II—Soft Gelatin Capsules of "The Theory and Practice of Industrial Pharmacy", pp. 404–420, Edition Lea & Fabiger (Philadelphia), 1976.

Casadio, "Tecnologia Farmaceutica", pp. 705–707, Edition Cisalpino Gogliardica (Milan), 1972.

Primary Examiner—Joseph L. Schofer
Assistant Examiner—Kathryne E. Shelborne
Attorney, Agent, or Firm—Steven P. Shurtz; Brinks Hofer Gilson & Lione

[57] ABSTRACT

The present invention deals with a pharmaceutical product in unit dosage form and a unit dosage drug delivery system which comprises a multiple layer capsule or housing having two or more layers, the layers being of materials, wherein the outer layer possesses a hydrophilic character and the inner layer possesses a hydrophobic character, and a capsule filling wherein one or more drug substances are admixed, dissolved, suspended or agglomerated in a hydrophobic support.

48 Claims, 3 Drawing Sheets

- FIRST OUTER HYDROPHILIC LAYER
- SECOND INNER HYDROPHOBIC FILM

- FIRST OUTER HYDROPHILIC LAYER
- SECOND INNER HYDROPHOBIC FILM
- THIRD INNER HYDROPHOBIC SHEATH WITH PORES

DRUG DELIVERY SYSTEM

The present invention relates to a unit dosage drug delivery system in the form of a soft capsule of different size, shape and colour, consisting of an external capsule housing having two or more coupled layers, sheaths or films, made from different materials, and of a capsule filling having one or more pharmacologically active drug substances for oral, rectal or vaginal administration, which are admixed, dissolved, suspended or agglomerated in an hydrophobic support, consisting basically of the main suspending agent "silicone resin" and optionally of one or more physiologically acceptable auxiliary ingredients, alike surfactants, disaggregants, linear or ramified aliphatic $C_2$–$C_3$ alcohols and their esters, retarding agents or other optional components, and to said pharmaceutical composition resulting thereof and to its method of preparation.

BACKGROUND OF THE INVENTION

Many attempts have been made in the past years to produce pharmaceutical forms, including some type of gelatin capsules and gelloids of gelatin, aiming to incorporate drug substances in the capsule filling, but the protection of the active ingredient has not been satisfactorily solved in case the used drug substance is degradable or unstable in presence of moisture, oxidizing agents or gastric (acid) fluid. Different types of gelatin capsules (hard or soft) have been studied by many authors, aiming to mainly protect the active ingredient against the atmosphere, but the results were partially satisfactory. A comprehensive review of different types of soft gelatin capsules has been reported by J. P. Stanley, Part II—Soft Gelatin Capsules of "The Theory and Practice of Industrial Pharmacy", pages 404–420, Edition Lea & Fabiger (Philadelphia), 1976 and by Casadio, "Tecnologia Farmaceutica", pages 705–707, Edition Cisalpino Gogliardica (Milan), 1972. Other authors have described conventional gelatin capsules in various patents as for example: U.S. Pat. Nos. 4,816,259; 3,656,997; 4,690,823; 5,173,304; 3,959,540; 3,432,594.

Described capsule housing conventionally possesses an external shell of which the basic ingredient is gelatin, and in general such capsule may be presented as either hard or soft gelatin capsule, the latter one containing suitable plasticizers. The shell of the conventional gelatin capsules consists of an unique external layer, having uniform composition and thickness, surrounding a capsule filling, which contains the pharmaceutical active drug substance admixed with suitable excipients. Few cases of an external film-coating layer have been also described. The unique external layer of the capsule shell of a conventional soft gelatin capsule contains basically gelatin, but also appreciable quantities of water as ingredient. However the presence of a certain amount of water in the conventional soft gelatin capsule housing constitutes a considerable seeking to formulate drugs or their salts, which are soluble in water or degradable in presence of moisture, or from the simple contact with water. In fact, by using the current ingredients and the known production techniques for conventional soft gelatin capsules, it is almost impossible to avoid the contact of the active drug substance, contained in the capsule filling, with the moisture of the gelatin mass of the external shell layer, either during the production steps or during the storage period of the finished capsule, until used for its intended purpose. Moreover, since the shell of the current soft gelatin capsules is containing, in addition to water, also large quantities of plasticizers (glycerol or sugars), conventional additives, including plasticizers, colouring agents, opacifiers and preserving agents, it is also difficult to satisfactorily prevent or to control possible chemical incompatibilities between the active drug substance incorporated in the filling and the ingredients of the capsule housing. Said ingredients may also enhance oxidation, degradation or hydrolysis processes, causing partial or sometime considerable loss of activity of the formulated active drug substance.

Accordingly, a main objective of the present invention is to provide an improved unit dosage drug delivery system in the form of a soft capsule, showing superior protection to the active drug substance from moisture, oxidizing agents, possible chemical interactions with other auxiliary or optional ingredients of the capsule housing, its method of preparation and the resulting pharmaceutical compositions of this invention.

SUMMARY OF THE INVENTION

It has now been surprisingly discovered that a unit dosage drug delivery system, having an external capsule housing made from at least two or more coupled layers, sheaths or films, from different materials, and a capsule filling made from "silicone resin", provides a substantially improved soft capsule system to incorporate many pharmaceutically active drug substances presenting formulation or stability problems.

It has further been discovered that such unit dosage drug delivery system: (a) offers to the pharmaceutical active drug substance, incorporated in the capsule filling, an improved protection from atmosphere, oxidation, moisture-induced hydrolytic or degradation processes, (b) permits a capsule filling moisture content less than 1%, (c) minimizes the diffusion of residual water from the external gelatin capsule housing to the capsule filling or of the water-soluble active drug substances to the outer housing system, (d) covers unpleasant tastes or odours, (e) controls or improves efficiently the site of action of the drug, (f) prolongs, when necessary, the release of the active drug substance from the capsule filling and (g) suitably avoids chemical incompatibilities between the active drug substance and the other auxiliary or optional ingredients.

Moreover it has further been observed that the unit dosage drug delivery system of this invention allows to conveniently formulate and deliver some delicate or unstable pharmaceutical drug substances, enhances the protective conditions of the relevant compositions thereof and prolongs also the period of stability of the formulated active drug substance.

TABLE 1

Conventional soft capsule compared with the unit dosage drug delivery system of this invention.
Omeprazole: oxidation process during the storage
(storage conditions: 6 month at 30° C., Relative Humidity 75% into an open container).

| Product | Colour change of the contained Omeprazole | |
|---|---|---|
| | Beginning | After 24 weeks |
| Conventional soft gelatin capsule (an unique layer capsule housing + Labrafils as suspending agent of the active drug substance) | white | violet-brownish |
| Unit dosage drug delivery system (multiple layers | white | white |

TABLE 1-continued

Conventional soft capsule compared with the
unit dosage drug delivery system of this invention.
Omeprazole: oxidation process during the storage
(storage conditions: 6 month at 30° C., Relative Humidity
75% into an open container).

| Product | Colour change of the contained Omeprazole | |
|---|---|---|
| | Beginning | After 24 weeks |
| capsule housing + silicone resin as suspending agent of the active drug substance + sodium lauryisarcosinate. 2 round) | | |

TABLE 2

Conventional soft capsule compared with the
unit dosage drug delivery system of this invention
containing the same active drug substance
Percentage of humidity after the process.

| Product | % of humidity of the capsule filling | |
|---|---|---|
| | Before capsulation process | After stabilization |
| Conventional soft gelatin capsule (an unique layer capsule housing + Gelucires as suspending agent of the active drug substance) | 0.23% | 3.80% |
| Unit dosage drug delivery system (multiple layers capsule housing + silicone resin as suspending agent of the actrve drug substance. 2 oval) | 0.08% | 0.11% |
| Unit dosage drug deiivery system (multiple layers capsule housing + silicone resin as suspending agent of the active drug substance. 20 oblong) | 0.07% | 0.12% |

In the conventional soft gelatin capsules, the humidity percentage, during the capsulation process and at the end of the stabilization process, is increased of 16.5 times, because of the water migration from the unique layer of the capsule housing to the capsule filling. This process results not important in the case of the unit dosage drug delivery system of this invention (1.3 times).

DETAILED DESCRIPTION OF THE INVENTION

Figure 1:
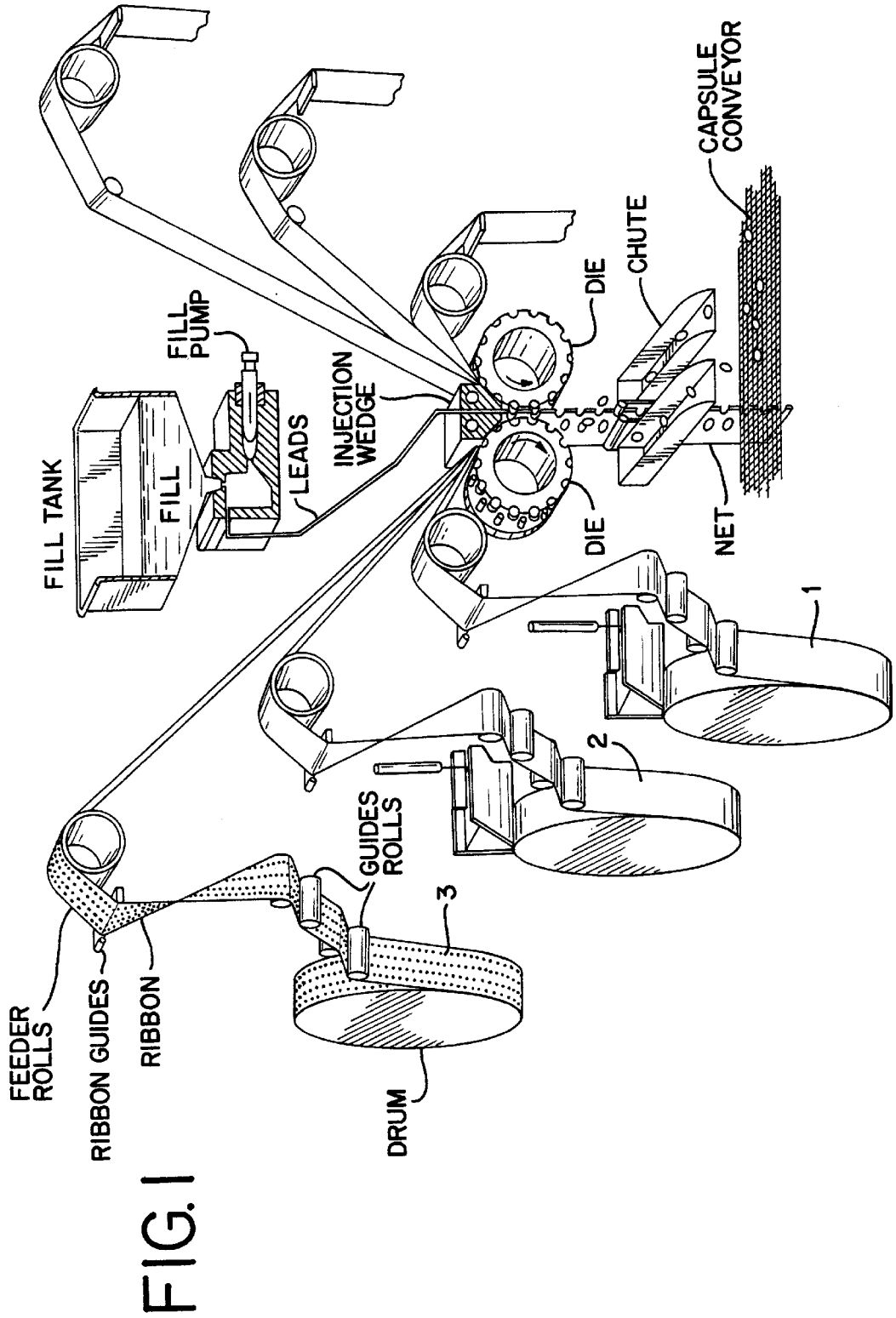
FIG. 1 is a schematic drawing of one embodiment of the process and apparatus used in the present invention.

The unit dosage drug delivery system, according to the instant invention, is a soft capsule having the shell housing consisting of at least two or more coupled layers, sheaths or films from different materials, the outer layer or sheath with hydrophilic character and the inner sheaths or films with hydrophobic character, and a capsule filling with a remarkable hydrophobic properties.

The first outer layer of the capsule housing (hydrophilic layer) is produced by admixing 45%–55% gelatin, 15%–30% glycerin or alternatively 15%–30% modified sorbitol solution at 45% or their mixture and 35%–40% water into a wet mass, which is thereafter processed into a gelatin ribbon (layer or sheath) of the desired width and thickness (preferably between 0.50 and 1 mm at the wet state) and, after a conventional drying and stabilization process, is containing 60%–70% gelatin, 20%–25% glycerin or modified sorbitol solution or their mixture thereof and 8%–10% water. During the production steps of the wet gelatin mass for the preparation of the first outer layer (hydrophilic layer), conventional additives, plasticizers, colouring agents, opacifiers, preserving agents, antioxidants may be optionally added to the molten mass admixture, without causing any detrimental effect to the resulting gelatin hydrophilic layer. The gelatin mass of the first outer layer is prepared with conventional methods, in a manner that produces a smooth completely dispersed and uniform gelatin molten suspension. The gelatin required for this dispersion should be preferably between 130 and 250 Bloom grams, alkali based skin or bone type, approved for food or pharmaceutical use. Also the other ingredients shall be of pharmaceutical or alimentary use quality, as it may be required by the regulatory authorities. The molten gelatin mass for the preparation of the first outer hydrophilic layer is cooled and passed on a suitable standard equipment, in order to conveniently prepare a ribbon of gelatin mixture, having the desired width and thickness. In another referred embodiment of this invention, the first outer hydrophilic layer of the capsule housing contains, instead of gelatin, other suitable compounds, alike polyphenyl compounds recently described in literature (Eisai, Korean patent appl. 90-10411 of Jul. 10, 1990), which may substitute gelatin for the manufacturing of conventional soft capsules. The production process is closely comparable to that used for the outer hydrophilic gelatin layer, as previously described. The first outer hydrophilic layer of this embodiment is present in the capsule housing in an amount of from 83.33% to 99.96% by weight, preferably between 90% and 98%.

The second inner hydrophobic film or sheath of the capsule housing of this invention consists of silicone, of silicone mixture or of other pharmaceutically acceptable silicone polymers of low-medium or medium-high density (silicone hydrophobic film or sheath), or preferably of silicone resin (silicone resin hydrophobic film or sheath), having a suitable intrinsic viscosity varying from 10 to 200,000 cSt ($mm^{2 \times S-1}$).

Silicones are well known polymers widely described in literature. There are different types of polysiloxanes, which are differentiated from the nominal viscosity, represented by an indication following the name of the substance. More conveniently one group of low-medium density silicones, used in the pharmaceutical and alimentary fields, are dimethyl polysiloxanes (also defined simethicone or dimethicone), which may be also conveniently used for the preparation of the second inner sheath or film of the capsule housing for its chemically inert and hydrophobic character. The most widely used dimethyl polysiloxanes (commonly defined in the European Pharmacopoeia, volume 11, page 138 as "dimethiconum" or "dimethicone" and in the French Pharmacopoeia 9.th edition as "low and medium density silicone oils") are dimethyl poiysiloxanes (polymers) of linear chain, having the following linear structural formula:

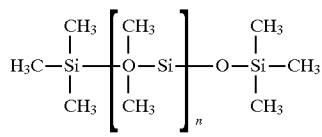

where the degree of polymerization may vary from n=20 to 400, while their nominal cinematic viscosity may vary from 10 mm$^{2 \times S-1}$ to 1000 mm$^{2 \times S-1}$ (from 10 cSt to 1000 cSt). Moreover dimethicone is a product commonly available on the market on its different grades of density. Pharmaceutical grade dimethicone is used for the silicone inner layer of this invention. The thickness of the second hydrophobic inner film or sheath of the capsule housing, made from silicone, silicone mixture or silicone resin, shall be comprised between 0.1 and 100 microns, preferably between 50 and 80 microns. The selected silicone or silicone mixture shall preferably have a consistence of grease or paste at a temperature of about 37° C. This second inner hydrophobic film or sheath is coupled with the internal face of the first outer hydrophilic layer or sheath, with the conventional methods disclosed in the production process.

In addition to the above components (layers, sheaths or films), the capsule housing may optionally contain an inner additional third or multiple films or sheaths, made from medium-high density silicone polymers or waxes or from jaluronic acid polymers, coupled with the internal face of the said second silicon sheath or film. Another preferred embodiment consists that the additional inner third or multiple films or sheaths are made from silicone waxes, which are non-toxic silicone derivatives, suitable for the preparation of paramedical, and pharmaceutical waxes, known under the trade mark VP 1622 (available from Wacker-Chemie Co) or silicone elastomers RP 73, conform to Pharmacopée Francaise "Silicones-Elastomères" (available from Rhone-Poulenc, Chemical Division, France). The thickness of the additional inner third or multiple films or sheaths of the capsule housing shall be comprised between 0.1 and 100 microns, preferably between 5 and 50 microns. These additional inner hydrophobic films or sheaths from silicone waxes shall be conveniently covered with pores, having a desired size (10–100 μm) and distribution (from 2,500 to 25 pores/mm$^2$), in order to achieve a retarded diffusion through the pores of the incorporated active ingredient. Another highly preferred embodiment of this invention is that the intrinsic viscosity value of silicone or silicone mixture of the second inner sheath or film of the capsule housing shall be lower than the intrinsic viscosity value of the silicone polymers or waxes of the optional inner third or multiple films or sheaths. More particularly embodiment of this invention is that silicone polymers or waxes and jaluronic acid polymers shall be have peremptorily a melting range of 39° C.–40° C. The sum of the second inner film or sheath and the optional inner third or multiple inner films or sheaths is further comprising of from 0.04% to 16.67%, preferably between 2% and 10% by weight of the entire capsule housing.

In a preferred embodiment of this invention, the capsule filling comprises one or more pharmaceutical active drug substances admixed, dissolved, suspended or agglomerated in "Silicone Resin", described in the monograph "Silicone Resin" from Japanese "Food Additives", page D-524, which is conveniently reported hereby.
SILICONE RESIN Description: Silicone Resin occurs as a white to light gray, transparent and semitransparent viscous liquid or paste substance without odour.

Identification: Determine the infrared absorption spectrum of Silicone Resin as directed in the liquid film method under the infrared spectrophotometry: it exhibits adsorbances at the wave number of about 2960 cm$^{-1}$, 1260 cm$^{-1}$, 1124–1010 cm$^{-1}$, and 800 cm$^{-1}$.

Purity: (1) After weight 15 g , put in Soxhlet's extractor. Extract 3 hours by 150 ml of Carbon Tetrachloride. Extraction liquid is evaporated on water bath and use it as test solution: n$_D^{25}$=1.400–1.410. (2) Viscosity of Extracted Silicone oil: 100–1,100 cSt (25° C.). (3) Specific Gravity: 0.96–1.02. (4) Silicon Dioxide (SiO$_2$): Remaining substance from the extraction should be under 2.25 g after one hour drying at approximately 100° C. (15%). A wide variety of pharmaceutical active drug substances may be incorporated into the capsule filling of this invention at different proportions, varying in the range of from 0.0001% to 45% by weight. These individual medicaments and drugs are from all major categories and therapeutic classes, without limitation for human and veterinary use, as for example oligopeptides, peptides, proteins, prostaglandins, cholesterol lowering agents, gastric antisecretories, antiacids, antiallergic agents, antiasthmatic agents, ACE inhibitors, diuretic agents, antineoplastic agents, antiviral nucleosides agents, antifungal agents, analgesics, non steroidal anti-inflammatories, antitussives, decongestionants, narcotics, antibiotics, cardiovasculars, central nervous system drugs, organic and inorganic salts, liophylized yeasts and vitamins. The drug is preferably micronized to produce a uniform capsule filling. Micronization is carried out by conventional technique.

The polypeptides, intended for use according to the present invention, is any peptide biologically useful in the cure, mitigation, treatment or prevention of diseases or in the enhancement of desirable physical or mental development and conditions in man or in animals. Polypeptides, especially proteins, for use in human and/or veterinary medicine are of particular interest for this invention due to their instability to the atmospheric agents, alike moisture and oxygen, which may cause their degradation and partial inactivation, which are therefore prevented from the unit dosage drug delivery system of this invention.

The polypeptides intended for use in the methods and compositions of the invention include molecules to which non-peptide prosthetic groups, such as carbohydrates, hemes and fatty acids, have been attached. The polypeptides include molecules made by living organisms or cells, molecules made by synthetic organic chemistry and molecules which are synthetically modified biological products. They may have an amino acid sequence identical to that of a natural substance or one altered by techniques such as site-directed mutagenesis.

In addition to the covalent (primary) structure, the polypeptides may possess unique conformation (combinations of secondary, tertiary and quaternary structure), which affects their biological functions and physical properties. The considered polypeptides may have important biological functions. They may act as enzymes, enzyme inhibitors, antibodies, antigens, transporters (transporters of electrons, oxygen, metal ions, or small organic molecules), ionophores, antibiotics, mitogens, hormones, growth regulators, neurotransmitters, cell surface recognition proteins, cell chemotactic factors, and cytotoxins. They may also be receptors, agonists, antagonists of the following: ionophores, mitogens, hormones, neurotransmitters, growth regulators, cell surface recognition proteins, cell chemotactic factors and cytotoxins.

Among the polypeptides contemplated by the present invention are therapeutically useful polypeptides such as anti-sera, anti-toxins and antigens and vaccines, including attenuated vaccines (such as those for cholera, influenza, meningitis, pneumonia, poliomyelitis, rabies, typhoid and staphyloccocus) and live vaccines (such as those for poliomyelitis, measles, rubella and mumps), growth factors, hormones and like bioactive peptides, as illustrated by α-1-antitrypsin, atrial natriuretic factor (diuretic), calcitonins, caimodulin, choriogonadotropin (α and β), colony stimulating factor, corticotropin releasing factor, β-endorphin, endothelial cell growth supplement, epidermal growth factor, erythropoietin, fibroblast growth factor, fibronectin, follicle stimulating hormone, granulocyte colony stimulating factor, growth hormone (somatotropin), growth hormone releasing factor (somatoliberin), insulin, insulin-like arowth factor (somatomedin), an interferon (typically α, β, γ), an interleukin (typically 1,2,3,4), lutropin, lymphotoxin, macrophage derived growth factor, macrophage inhibiting factor, macrophage stimulating factor, megakaryocyte stimulating factor, nerve growth factor, pancreatic endorphin, parathyroid hormone, platelet derived growth factor, relaxin, secretin, skeletal growth factor, superoxide dismutase, thymic hormone factor, thymic factor, thymopoeitin, thyrotropin, transforming growth factor (α and β), tumor necrosis factor, tumor angiogenesis factor, vasoactive intestinal polypeptides and wound angiogenesis factor, immunosuppressives, such as RhO (D) ISG and IVGG's, thrombolytics such as urokinase, streptokinase and tissue plasminogen activator, and antigens such as Rhus all (poison ivy), Rhus tox poison ivy-polyvalent and staphage lysate (staphyloccocus lysate).

Other highly preferred polypeptides for use in accordance with this invention are cyclosporins, a group of biologically active metabolites produced by Tolypociadium inflatum Gams (formally designed as Trichoderma polysporum) and other fungi imperfecti. The major component, cyclosporin A, is a non-polar cyclic oligopeptide with selective immunosuppressive activity very suitable after human organ transplants.

Other polypeptides contemplated by this invention are poiypeptides specifically intended for veterinary use, including vaccines, animal growth factors and bovine interferons and interleukin-2. Illustrative vaccines include: bovine vaccines (for example those for anthrax, clostridium (multiple species), pasteurelia, leptospira pomona, bovine diarrhoea, brucellosis, parainfluenza, 3-respiratory syncytial virus, tetanus, vesicular stomatitis and staphylococcus), canine vaccines (for example those for bordetella, coronavirus, distemper, parvovirus, parinfluenza and rabies), equine vaccines (for example those for anthrax, encephalomyelitis, influenza, tetanus, rabies and streptococcus-strangles), feline vaccines (such as those for leukemia, pneumonitis-chlamydia and rabies), ovine vaccines (for example those for anthrax, blackleg, bluetongue, anerotoxemia, tetanus and vibriosis) and porcine vaccines (for example those for anthrax, enterotoxemia, dysentery, erysipelas, leptospirosis, parvovirus, pseudorabies, tetanus and rotavirus).

Yet other polypeptides contemplated for use herein are polypeptides of particular interest in the field of medicine are various enzymes. The enzymes can include labelling enzymes, modifying enzymes, nucleases, polymerases, sequencing enzymes and restriction enzymes. Highly preferred enzymes of the instant invention are lysozyme and digestive enzymes, alike pepsin, enterokinase, trypsin, chimotrypsin, carboxypeptidase, aminopeptidase and elastase (pancreatopeptidase).

Preferred poiypeptides for use in accord with the instant invention include growth regulators. Among the preferred growth regulators are hematopoietic factors (which affect the maturation and proliferation of blood cells in lymphoid tissue and bone marrow), cytokines (which generally influence eukaryotic cell growth) and lymphokines (which affect lynphocyte growth). Specific polypeptides, which are growth regulators or lymphokines, are: interleukin 1,2,3 and 4; α, β, and γ interferons; granulocyte colony stimulating factor (G-CSF); granulocyte-macrophage CSF (GM-CSF); macrophage CSF (m-CSF); megakaryocyte CSF; multi CSF or IL-3 (also known as BPA, HCGF,MCGF and PSF); erythropoietin; lymphotoxin; tumor necrosis factor (TNF, also known as cachectin); α and β transforming growth factor (TGF); nerve growth factor (NGF); insulin-like growth factor I and II (IGF I is also called somatomedin C); growth hormone (GF, also called somatotropin); and growth hormone releasing factor (GHRF, also called somatoliberin). See Clark et al, "The human Hematopoietic Colony Stimulating Factors", Science, 1229–1237 (Jun. 5, 1987); Tanniguchi, "Regulation of Cytokine Expression", Ann. Rev. Imm., 6, 439–464 (1988); and Watson et al., Molecular Biology of the Gene, Vol. II, 4 th Ed., Benjamin/Cummings Publishing (1987).

In another preferred embodiment of this invention, the drug substance consists of prostaglandins, alike prostaglandin $A_1$, prostaglandin $D_2$, prostaglandin $D_2$ analogs, prostaglandin $E_1$, keto prostagiandin $E_1$, prostaglandin $E_2$, methyl prostaglandin $E_2$, prostaglandin $E_3$, prostaglandin $E_{1\alpha}$, prostaglandin $F_{2\alpha}$, methyl prostaglandin $F_{2\alpha}$, prostaglandin $F_{3\alpha}$, prostaglandin H series, prostaglandin X series; prostaciclins, alike prostagiandin $I_2$, carba prostaglandin $I_2$, oxo-prostaglandin $I_2$, and their pharmaceutically acceptable salts or series derivatives, alike misoprostol; tromboxanes, which are hygroscopic and oxidable and their derivatives, alike ifetroban sodium ($TXA_2$/prostaglandin endoperoxide receptor antagonist), used as antithrombotic agents.

Similarly in another preferred embodiment, the drug substance is consisting of elcosapentasnoic acid (referred also as EPA) and docosahexanenoic acid (referred also as DHA), fatty acids, which are unstable by action of light and oxygen, formulated alone or added with tocopherol as antioxidant.

In another preferred embodiment the drug substance is represented by $H^+/K^+$ ATPase inhibitors (benzimidazole derivatives and their pharmaceutically acceptable salts) alike omeprazole, lansoprazole, pantoprazole, pantoprazole sodium, timoprazole, rabeprazole sodium (pariprazole sodium? and other published products under research (search codes: NC-1300, TY-11345), which are not stable in gastric juice and readily oxidable, with macroscopic changes of colour from white to violet-brownish and consequent loss of activity.

Another embodiment for the drug substance capsule filling consists of $H_2$-antagonists, alike ranitidine hydrochloride and base, nizatidine, famotidine, which are degraded by atmospheric moisture.

In another preferred embodiment of the unit dosage drug delivery system of this invention, the drug substance consists of antiacids inorganic salts, alike sodium bicarbonate, calcium carbonate and magnesium carbonate. In another preferred embodiment, the drug substance consists of orally active antiallergic agents, alike astemizole, terfenadine, tranilast, loratadine, azelastine, amlexanox, repirinast, tarzanolast pemiroiast potassium batebulast HCl, quinolast sodium, suplatast tosylate and other published products under research (search codes: Cl-949, KW-4679, TYB-2285)

In another preferred embodiment of the unit dosage delivery system of this invention, the drug substance consists of antiasthmatic agents, alike ketotifen, fluoxetine, clemastine fumarate, cetirizine and theophyllinic agents, alike ambuphylline, bamiphylline and oxpentiphylline.

In another preferred embodiment the drug substance consists of orally active inhibitors of angiotensin converting enzyme (ACE), alike captopril, enaiapril, lisinopril and trandolapril. which have an unpleasant odor and scarce stability.

In another preferred embodiment the drug substance consists in diuretic agents, alike indapamide and other aminosulfonic derivatives.

In another preferred embodiment of the unit dosage delivery system of this invention, the drug substance consists of antineoplastic agents, alike etoposide and estramustine phosphate sodium.

In another preferred embodiment the drug substance consists of immunopotentiator agents, alike levamisole.

In another preferred embodiment the drug substance consists of antiviral nucleosides agents, alike acyclovir with inhibitory activity towards several herpes viruses and zidovudine, stavudine, didanosine, for the treatment of adult patients with HIV infection or paediatric patients (three months to 12 years) with symptomatic HIV infection or with significant HIV-related immunosuppression.

In another preferred embodiment of this invention, the drug substance consists of oral antifungal agents, alike terbinafine, amorolfine, ketoconazole, fluconazole, itraconazole and cilofungin.

In another preferred embodiment of the unit dosage delivery system of this invention, the drug substance consists of antiparkinson agents, alike selegiline, inhibitor of Monoamino-oxidase B (MAO B), and pergolide mesylate, pharmacologically active as dopamine agonist.

In another preferred embodiment of this invention, the drug substance consists of anticonvulsant-antiepileptic agents, alike vaiproic acid, lamotrimine and felbamate.

In another preferred embodiment the drug substance is represented by antiinflammatory, analgesic, antipyretic agents, which have ulcerative side-effects: aspirin (acetyl salicylic acid), derivatives of indol, alike indomethacin and sulindac, derivatives of oxicam, alike piroxicam and tenoxicam, derivatives of propionic acid, alike pirprofen, ibuprofen, flurbiprofen, ketoprofen, diclofenac, ketorolac, naproxen and indoprofen.

In another embodiment of the unit dosage delivery system of this invention, the drug substance consists of finasteride, an agent used in case of prostatic hyperthrophy.

In another preferred embodiment of this invention, the drug substance consists of calcium blocking agents, alike nifedipine, isradipine, nicardipine, nicardipine, nimodipine, nisoldipine, furaldipine, clinidipine, efonidipine, elnadipine, amlodipine, nitrendipine, palonidipine, elgodipine, manidipine, benidipine, cronidipine, barnidipine, oxidipine, perdipine, niguldipine, nilvadipine, lacidipine, lidoflazine, cinnarizine, flunarizine and other published products under research, alike darodipine (EN: 090658), arandipine (MPC-1304) and pranidipine (OPC-13340).

In another preferred embodiment of the unit dosage drug delivery system, the drug substance consists of cardiovascular preparations, alike nicorandil or diltiazem. In another preferred embodiment of the unit dosage drug delivery system of this invention, the drug substance is represented by lyophylized yeasts, alike lactobacillus bifidus and lactobacillus bulgaricus, which are not stable in gastric juice. Other optional components in convenient amount may be added to the capsule filling of the instant invention, alike surfactants, such a sorbitan derivative (e.g. polysorbate 80) or sodium lauryl sarcosinate, additional micronized silica gel or lecithin, antioxidants and $C_2$–$C_3$ linear or ramified alifatic alcohols, such as absolute ethanol, or polyalcohols and their $C_1$–$C_2$ esters.

The antioxidant is hindered phenol, retinoic acid, erythorbic acid, tocopherol, citric acid, and/or anthraniiic acid, preferably a retinol acid derivative such as retinol, retinoic acid or its fatty acid esters especially retinyipalmitate. The antioxidant is present at concentrations further comprising of from 0.001% to 5.0%, preferably 0.3%–0.8% by weight of the capsule filling. The surfactant concentration may vary from 0.1% to 2.0% by weight of the capsule filling. The alcohol or polyalcohol content shall be considered of from 1% to 30%, preferably from 10% to 25% by weight of the capsule filling. Minor amounts of other materials may be added at art established leveis. These include, without limitation, pigments, opacizers, aromes, sweeteners and the like materials, when added, should not interfere with the active drug substance of these compositions, The above optional components or modifications of the capsule filling, consisting basically of drug substance and "Silicone Resin", are intended to improve the acceptability, but are well known within the skill of workers in the pharmaceutical arts and, by themselves, constitute no part of the present invention.

In another preferred embodiment of the unit dosage drug delivery system of this invention consists of rendering gastroresistant the capsule housing after the production process or after any period of storage. The capsule housing of the instant invention, which has been modified to be rendered gastroresistant, presents for some drug substances the advantage that the capsule filling with the incorporated active drug substance is released (disintegrated) in the intestines, after passing unchanged through the stomach. The techniques used for rendering gastroresistant the soft capsules of the instant invention are very close to those already used for the tablets or gelatin capsules and are within the skill of workers in the pharmaceutical arts and, by themselves, constitute no part of the present invention. The gastroresistance may be obtained by different known methods, according with the specific material of the first outer hydrophilic layer or sheath. Different methods have been also described to produce gastroresistant conventional soft gelatin capsules. Mercer immersed twice the capsules in a solution of beeswax (10% in ether) and then in multiple baths of molten salol (Mercer J., Austral. J. Pharm., 36,1169, 1955). Carstensen treats firstly the conventional soft gelatin capsules with a solution at 5% of HCl and at 5% of water in isopropanol to have a shiny surface through an hydrolysis. After drying, they are passed in a solution of 3% of ethylcellulose in isoamyl alcohol. Finally the gelatin capsules are dried by centrifugation (Carstensen J. T., et al., U.S. Pat. No. 2,789,920, Apr. 23, 1957). In British Patent 602,260 the solution of gelatin in aqueous glycerin is added with insoluble organic and inorganic salts of cellulose acetate phtalate. The pH of the film shall necessarily be 7–7.5. The capsules may be then treated with a solution of 1% of formaldehyde and then washed and dried. To obtain the gastroresistance, Yen and Stirn immerse, for one minute, under stirring, the capsules in an ethanolic solution of 0.5%–10% of formalin, 0.25% of resins, alike benzoin and 0.5 %–3% of cumarin or vanillin. The solution is eliminated by centrifugation and the capsules are dried (Yen E. C., Stirn F. E., U.S. Pat. No. 2,727,833,20, Dec. 20, 1955). The unit dosage drug delivery system of this invention may be also conveniently treated with a solution of aldehyde, preferably formaldehyde, in dispersion in a highly volatile watermiscible solvent, preferably acetone. This treatment may be carried out by immersion or by spraying, but preferably by sprinkling the capsules. The ratio of 30% formaldehyde to acetone is 1:60. The formaldehyde content of the solution is checked at the beginning of the operation and during the process. For this control, may be used the Bougault and Gros method (oxidation with iodine and titration on return of the excess of iodine). The treatment with formaldehyde may be done in order to avoid washing and drying the soft capsules, depending on the degree of gastroresistanre and the time of opening in the intestinal juice. The application is obtained in a turbine used for making pills, where internally there are driving, guiding and acceleration devices for the rotation of the capsules, which are sprinkled by the admission of the solution by means of nozzles or sprinkling roses, opening into the chamber of the turbine. In this manner, the capsules are well wetted by the dispersion of formaldehyde, the acetone evaporates rapidly for the presence of a suction device and the capsules can be immediately packed. Another known method for soft gelatin capsules consists to immerse or spray the first outer hydrophilic layer or sheath for a suitable period with tannic acid, thus the modified gelatin of the first outer layer or sheath conveniently presents suitable gastroresistant properties, which allow the capsule housing to be disaggregated only in intestinal juice. In case the first outer layer is made from other suitable not gelatinous material, alike polyphenyl compounds, the gastroresistance can be achieved applying to the capsule housing a suitable coating composition, as known in the art, to produce stable capsules, resistant to the acid secretions of the stomach and dissolved in the alkaline fluid of the intestinal secretions. The gastroresistance control method is indicated in USP XXII, (page 1577–1578). This method is consisting of putting the capsules in artificial gastric juices for one hour, then in artificial intestinal juices and of measuring the time of disaggregation in this latter liquid.

Another more particularly embodiment of the unit dosage drug delivery system of this invention consists of extending the dissolution rate of the active drug substance over a wide range of time, by incorporation in the silicone resin of one or more release modifying substances. This is a particularly advantageous feature, as it allows the release rate to be modified as desired and to provide a suitable controlled dissolution rate of the active drug substance. Suitably pharmaceutical grade excipients, which produce an extended rate of dissolution, include hydrophobic release modifying substances, such as the following or mixture thereof: beeswax, silicone waxes and natural or modified stearic acid, paimitic acid, myristic acid, lauric acid, stearyl alcohol, cetyl alcohol, glyceryl stearate, ethyl oleate, arachids oil, cotton seed oil, rape seed oil, liquid paraffin, polyethylene glycol (from 400 to 20,000), mono-, di- and/or triglycerides such as Miglyols (trade mark), Labrafils (trade mark), Precirols (trade mark) and Gelucires (trade mark). The quantity of the release modifying substances, incorporated into the silicone resin, depends on their nature and on the required release properties. More particularly the level of the release modifying substances is further comprising of from 15% to 60%, preferably between 20% and 55% by weight of the silicone resin of the capsule filling. The release modifying substances may be incorporated in the silicone resin by admixing, dissolving, suspending, agglomerating, homogeneizing or melting them together. The extended release control method is indicated in USP XXII (page 1580).

PRODUCTION PROCESS

The production process is conveniently carried out in air-conditioned areas to assure the proper conditioning (drying) of the multiple layers, capsule housing, of the capsule housing, the protection of the capsule filling to preserve low moisture content of active drug substances and their mixtures thereof. More particularly the temperature range in the areas is 15° C.–24° C. (60° F.–75° F.) and the humidity is 20%–40%.

In the capsule housing preparation department, are individually weighed the solid elements of the multiple layers, sheaths or films, mixed with accurately metered and chilled (at about 8° C./45° F.) liquid elements. Then the resulting masses of each layer, sheath or film are individually transferred to separate melting tanks, where are melted, under stirring and vacuum (from 730 to 750 mm Hg) at about 90° C. (200° F.) of temperature. The operations are carried out simultaneously in conventional mixers, for example mixers of stainless steel or similar material. To the mass of the first outer hydrophilic layer or sheath conventional additives, including colouring agents, plasticizers, opacifiers and preserving agents and antioxidants may be added. Usually for each mixing process it is necessary 25 minutes and for melting procedure about 2 hours. At this moment, a sample of the resulting mass of the first outer layer is taken and compared visually against a colour standard; if adjustments are required, more colorants are added. The masses of each layer, sheath or film are maintained in different mixers at a temperature of 57° C.–60° C. (135° F.–140° F.), before and during the capsulation process. The materials preparation department will have a weighing and mixing area equipped with the necessary equipment and facilities for the preparation of a variety of fill mixtures, that may be encapsulated. An initial blending of the capsule fill ingredients (basically active drug substance, silicone resin and other solids and liquids) is completed in suitable stainless steel, jacketed tanks and mixers. When the above step is completed, the masses are individually subjected to a milling or homogenizing process (homoloid mill, stone mill or hopper mill may be conveniently used as equipment), not to reduce the particle size, but to break up agglomerates of solids and to ensure that all ingredients are suitably wetted with the liquid carrier. In case of extended release preparation, the release modifying substances are admixed, dissolved, suspended, agglomerated or melted together to the above mixture at this stage. Then the resulting capsule fill is subjected to de-aeration to achieve uniform capsule fill weight and protection from the oxidation before and during capsulation. It is convenient sending samples of the mixture fill to the control laboratories for various tests, alike ingredients assays, homogeneity tests, moisture content and air entrapment. After quality approval, the capsule fill is transferred from the mixing tank to the fill tank. the container that will be used at the capsulation machine. In order to better describe the fundamental aspects of the instant invention, a schematic drawing of the same production process is presented in FIG. 1; the mass of the first outer hydrophilic layer is fed by gravity to a spreader box and the flow of this mixture, on to rotating drum (1), cooled at 13° C.–15° C. (56° F.–58° F.) of temperature, is obtained by gravity or under pressure. The first outer layer or sheath, obtained with a controlled thickness, is fed over guide rolls and then down, between the injection wedge and the die rolls. On the same fashion, the second and the additional inner films or sheaths (made from silicone or silicone mixture), are individually obtained and coupled with the internal face of the first outer layer or sheath, by passing them between the wedge and the die rolls to obtain the capsule housing. In FIG. 2 is presented an alternative method of capsulation process, where the second rotating drum (2) is replaced by a spreader Uox. The spreader box is installed on the top of the first rotating drum and deposits directly, by gravity or under pressure, the second hydrophobic sheath or film of the desired thickness on internal face of the outer layer or sheath. Any additional inner layer or sheath is then obtained and incorporated to the capsule housing as previously described. The capsule filling, to be capsulated, flows by gravity from the fill tank into a positive displacement pump and then, accurately metered by this pump, through the leads and the wedge, into the capsule housing (made from multiple coupled layers, sheaths or films), between the die rolls. In the bottom of the wedge, there are small orifices, lined up with die pockets of the die rolls. The capsule is about half sealed, when the pumped material forces the various films into the die pockets, where the capsules are filled, shaped, and hermetically sealed and cut from the ribbons. The sealing of the capsule is obtained by mechanical pressure on the die rolls and the heating (37° C.–40° C.) of the capsule housing by the wedge; thus the capsules can be preliminary dried or spread directly on trays and placed in drying tunnels. The capsules are air-conditioned in area having 20% to 30% of relative humidity and 20° C. –24° C. (70° F.–75° F.) of temperature. At the end of the manufacturing process, the soft capsules of the invention are sent to the inspection department and held until released by the quality controls. Control tests specifically applicable are: seal thickness determinations, moisture tests, fragility or rupture tests, and determination of freezing and high temperature effects. The determination of dosage weight for the content of the drug substance shall be also controlled as indicated in USP XXII. They may be stored for long periods without any sign of degradation or decomposition. Immediately before or after any period of storage, when necessary, the soft capsules can be sent to a gastroresistance department and processed, with methods as described before.

Figure 3A:
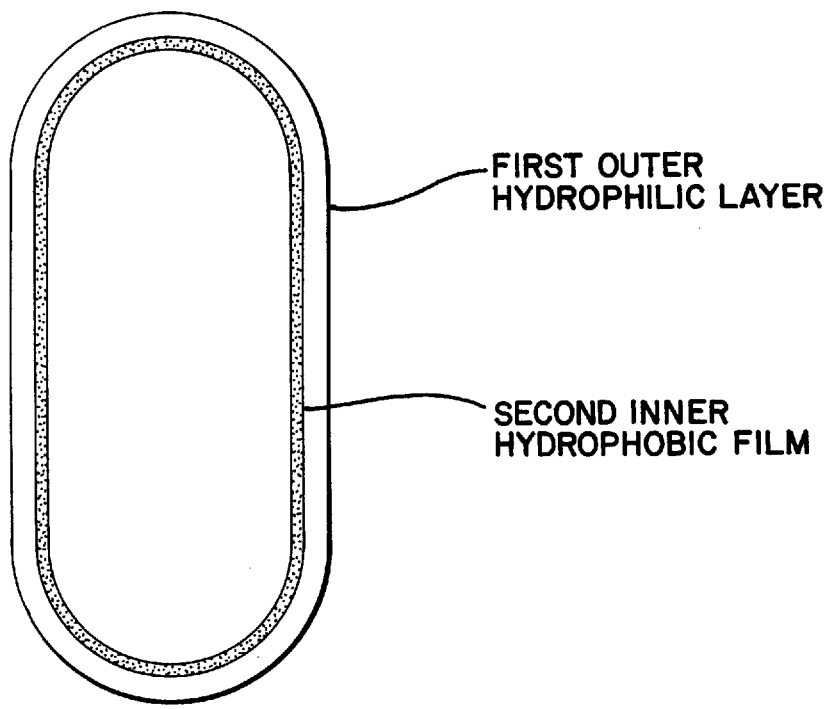
FIGS. 3A and 3B are cross sectional diagrams of the product of the present invention.
Figure 3B:
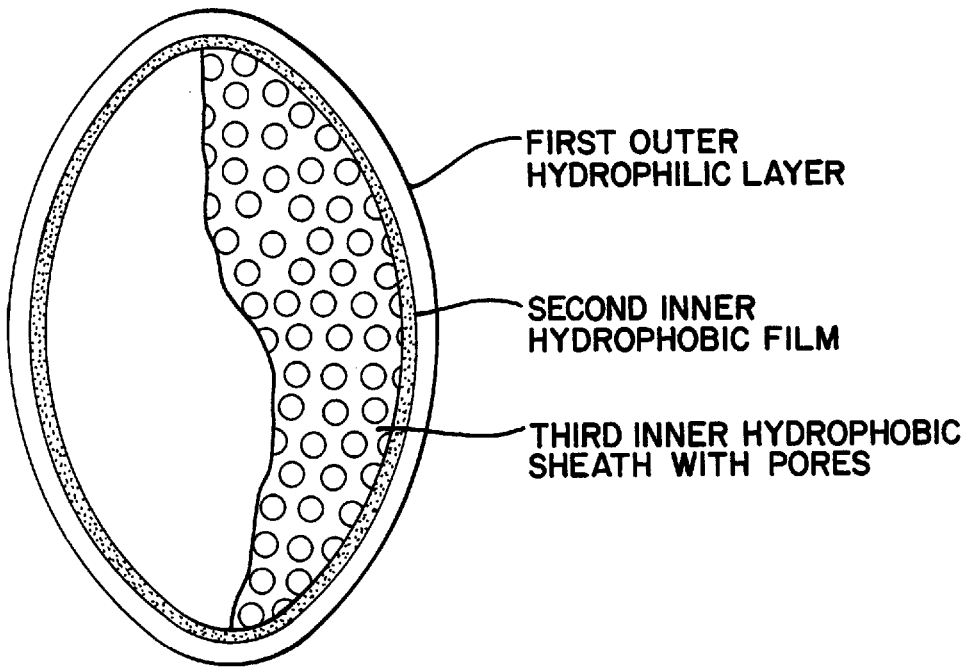

The difference of the soft gelatin capsules of the prior art and of the unit dosage drug delivery system of this invention is further evidenced by the illustration of FIG. 3A and 3B, showing cross section diagrams of the claimed product. The new soft capsules of invention have excellent pharmaceutical properties and acceptability. They are chemically and physically stable and do not develop significant pH variation during storage. It is surprising that the new pharmaceutical soft capsules of this invention, manufactured from coupled multiple layers, sheaths or films, incorporating a mixture of active drug substances and silicone resin, are considerably more stable and present an improved protection from adversely affecting agents, alike atmosphere, moisture and oxidation and substantially prevent the diffusion of the residual water contained from the capsule housing to sensitive active drug substance incorporated in the capsule filling. In order to better illustrate the instant invention, the following examples are reported, that in any case may not be considered limitative.

EXAMPLE 1

Preparation of 9,100 soft capsules of cyclosporin 25 mg (2 oval)

Each soft capsule containing

| CAPSULE FILLING | |
| --- | --- |
| cyclosporin | 25.000 mg |
| silicone resin (viscosity 100 cSt) | 50.000 mg |
| absolute ethanol | 25.000 mg |
| Total weight of the content | 100.000 mg |
| CAPSULE HOUSING | |
| First outer layer | |
| gelatin | 49.230 mg |
| glycerol | 26.263 mg |
| Second inner layer: | |
| silicone (viscosity 125 cSt) | 3.720 mg |
| Total weight of the capsule housing | 79.213 mg |

Capsule housing/first outer layer 448 g of gelatin, 239 g of glycerol and 494 g of water are mixed. This mixture is melted under vacuum (730–750 mm Hg) and stirring in a stainless steel tank at a temperature between 75° C. and 80° C., until the melting is absolutely complete. The opaque mass, thus obtained, is then used for making the first outer layer ribbon (wet thickness about 0.76 mm), in the manner described before (FIG. 2/Drum 1).

Capsule housing/second inner layer 33.85 g of silicone, having an intrinsic viscosity of about 125 cSt, are placed in a spreader box installed on the top of the rotating drum 1, that deposits continuously on the internal surface of the first outer gelatin ribbon, an uniform film, thickness about 50 $\mu$m (FIG. 2).

Capsule filling 455 g of silicone resin, having a viscosity of 100 cSt, are mixed with 227.5 g of cyclosporin (100% assay) and 227.5 g of absolute ethanol, until complete homogeneity. The suspension thus obtained is loaded, under constant stirring, into the fill tank of the fill pump of the machine for the production of soft capsules (FIG. 2). The wet soft capsules are then dried and stabilized according to conventional methods on trays, placed in drying tunnels (72 hours at 20° C.–25° C.). 7,470 soft capsules pass the visual inspection and the control tests. Yield: 82.08%.

EXAMPLE 2

Preparation of 16,250 soft capsules of captopril 25 mg (2 round).

Each soft capsule containing

| CAPSULE FILLING | |
| --- | --- |
| captopril | 25.000 mg |
| silicone resin (viscosity 150 cSt) | 75.000 mg |
| Total weight of the content | 100.000 mg |
| CAPSULE HOUSING | |
| First outer layer | |
| gelatin | 49.280 mg |
| modified sorbitol solution 45% | 26.320 mg |
| titanium dioxide E 171 | 0.798 mg |
| iron oxide red E 172 | 0.020 mg |
| Second inner layer: | |
| silicone (viscosity 200 cSt) | 4.807 mg |
| Total weight of the capsule housing | 81.225 mg |

Capsule housing first outer layer 800.8 g of gelatin, 427.7 g of modified sorbitol solution 45% (in water), 715.0 g of water, 12.97 g of titanium dioxide (E 171), 0.325 g of iron oxide red (E 172) are conveniently mixed, under vacuum (730–750 mm Hg) in a stainless steel tank at a temperature between 75° C. and 80° C., until the melting is homogeneous and complete. The resulting pink mass is then used for preparing the first outer layer ribbon (wet thickness about 0.82 mm) on the fashion already described.

Capsule housing/second inner layer 78.11 g of silicone, viscosity about 200 cSt, are introduced in a spreader box, placed on the top of the rotating drum 1. In this manner, in the internal face of the first outer layer is deposited an uniform film with a thickness of about 65 μm.

Capsule filling 1,219.0 g of silicone resin, having a viscosity of 150 cSt, are added to 406.25 g of captopril (adjusted to 100% titre) in a suitable mixer and the suspension is loaded into the fill tank of the fill pump of the capsule machine for the production of soft capsules (FIG. 2). The resulting wet soft capsules are dried and stabilized according to conventional methods on- trays, placed in drying tunnels (60 hours to 28° C.–30° C.). 13,100 soft capsules pass the visual inspection and the control tests. Yield: 80.6%.

EXAMPLE 3

Preparation of 32,500 soft capsules of lysozyme hydrochloride 250 mg (20 oblong)

Each soft capsule containing

| CAPSULE FILLING | |
| --- | --- |
| lysozyme hydrochloride | 250.000 mg |
| silicone resin (viscosity 125 cSt) | 850.000 mg |
| Total weight of the content | 1100.000 mg |
| CAPSULE HOUSING | |
| First outer layer | |
| gelatin | 261.154 mg |
| glycerol | 139.384 mg |
| titanium dioxide E 171 | 9.230 mg |
| Second inner layer: | |
| silicone (viscosity 250 cSt) | 36.077 mg |
| Total weight of the capsule housing | 445.845 mg |

Capsule housing/first outer layer 8.49 Kg of gelatin, 4.53 Kg of glycerol, 0.3 Kg of titanium dioxide (E 171) and 9.38 Kg of water are mixed thoroughly and the mixture is melted in a stainless steel tank, under vacuum and constant stirring, at a temperature between 75° C. and 80° C. When the melting is completed, the mass is used for preparing the first outer layer ribbon on the fashion already described, having a thickness of about 0.96 mm.

Capsule housing/second inner layer 1,172.0 g of silicone, having an intrinsic viscosity of about 250 cSt are placed in a spreader box, installed on the top of the rotating drum 1, that dispensed continuously on the internal surface of the first outer gelatin ribbon an uniform film, having a thickness of about 60 μm (FIG. 2).

Capsule filling 27.625 Kg of silicone resin, having a viscosity of 125 cSt, are mixed with 8.125 Kg of lysozyme hydrochloride (100% assay) and the obtained paste is loaded, under pressure into the fill tank of the fill pump of the machine for the production of the soft capsules (FIG. 2). The wet soft capsules are then dried and stabilized according to conventional methods on trays, placed in drying tunnels (80 hours at about 25° C.). 24,520 soft capsules pass the visual inspection and the control tests. Yield: 75.44%.

EXAMPLE 4

Preparation of 24,000 gastroresistant soft capsules of lansoprazole 30 mg (2 oval).

Each gastroresistant soft capsule containing

| CAPSULE FILLING | |
| --- | --- |
| lansoprazole | 30.000 mg |
| silicone resin (viscosity 250 cSt) | 69.250 mg |
| sodium laurylsarcosinate | 0.750 mg |
| Total weight of the content | 100.000 mg |
| CAPSULE HOUSING | |
| First outer layer | |
| gelatin | 49.250 mg |
| modified sorbitol solution 45% | 12.916 mg |
| glycerol | 13.333 mg |
| titanium dioxide E 171 | 9.351 mg |
| Ponceau red (FD & C Red n°1/E 124) | 0.418 mg |
| quinoline yellow (E 104) | 0.025 mg |
| Second inner layer | |
| silicone (viscosity 300 cSt) | 9.121 mg |
| Total weight of the capsule housing | 85.414 mg |

Capsule housing/first outer layer 1,182.0 g of gelatin, 310.0 g of modified sorbitol solution 45% (in water), 320.0 g of glycerol, 1,200.0 g of water, 8.43 g of titanium dioxide (E 171), 10.03 g of Ponceau red (FD & C Red. n°/E 124), 0.6 g of quinoline yellow (E 104) are conveniently mixed, under stirring and vacuum (730–750 mm Hg), in a stainless steel tank at a temperature between 75° C.–80° C., until the melting is complete. The red gelatin mass is utilized to obtain the first outer layer ribbon (wet thickness about 0.75 mm) by a process as previously described.

Capsule housing/second inner layer 218.91 g of silicone, having a viscosity of about 300 cSt, flow by gravity in a spreader box on the top of the rotating drum 1, that continuously deposits an uniform film, with a thickness of about 80 μm, in the internal face of the first outer layer.

Capsule filling 1,662.0 g of silicone resin, with a viscosity of 250 cSt, are mixed with 720.0 g of lansoprazole (100% assay) and 18 g of sodium laurylsarcosinate. The resulting suspension is placed in the fill tank of the fill pump of the capsule machine for the production of the soft capsules. The soft capsules are manufactured in the usual manner as described in FIGS. 1 and 2. The resulting wet soft capsules are dried and stabilized, according to conventional methods on trays, placed in drying tunnels (72 hours at 20° C.–25° C.). 19,407 soft capsules pass the visual inspection and the control tests. Yield: 80.86%.

Gastroresistance process

The above soft capsules are employed for the preparation of gastroresistant capsules by proceeding on the following fashion: a conventional quantity of capsules (about 10,000) are introduced in a turbine (or rotating pan). By means of a tube connected with a tank, containing formaldehyde dispersion in acetone in the ratio of 1:60 (formaldehyde at 30% potency in acetone), the soft capsules are sprayed by using 503.3 g of this dispersion. The formaldehyde is immediately fixed by the first outer hydrophilic layer and the acetone is simultaneously evacuated by a suction devices provided inside the turbine (or rotating pan). The soft capsules are packed individually in blisters.

The gastroresistance of 2 hours (measured according to USP XXII pages 1577–1578) was reached 4 days after treatment, being made as a function of the ageing of the capsules. The time of opening of gastroresistant soft capsules in the artificial intestinal juice, for an ageing of 2 months to one year, is practically constant at 200 seconds.

EXAMPLE 5

Preparation of 26,000 extended release soft capsules of nicorandil 45 mg (2 oval).

Each extended release soft capsule containing

| CAPSULE FILLING | |
| --- | --- |
| nicorandil | 45.000 mg |
| silicone resin (viscosity 300 cSt) | 55.000 mg |
| Total weight of the content | 100.000 mg |
| CAPSULE HOUSING | |
| First outer layer | |
| gelatin | 49.269 mg |
| modified sorbitol solution 45% | 26.307 mg |
| titanium dioxide E 171 | 0.800 mg |
| iron oxide red E 172 | 0.040 mg |
| Second inner layer | |
| silicone (viscosity 100 cSt) | 6.322 mg |
| Third inner layer | |
| silicone elastomer (with pores) | 4.353 mg |
| Total weight of the capsule housing | 87.091 mg |

Capsule housing/first outer layer 1,281.0 g of gelatin, 684.0 g of modified sorbitol solution 45% (in water), 20.8 g of titanium dioxide (E 171), 1.04 g of iron oxide red (E 172) and 900 g of water are conveniently mixed, under vacuum and stirring, in a stainless steel tank at a temperature of 75° C.–80° C. The pink gelatin mass is utilized to obtain the first outer layer ribbon (wet thickness about 0.76 mm), by a process as previously described.

Capsule housing/second inner layer 164.37 g of silicone, having a viscosity of about 100 cSt, are introduced in a spreader box, placed on the top of the rotating drum 1. In this manner on the internal face of the first outer layer is deposited an uniform film with a thickness of about 55 μm (FIG. 2).

Capsule housing/third inner layer

Figure 2:
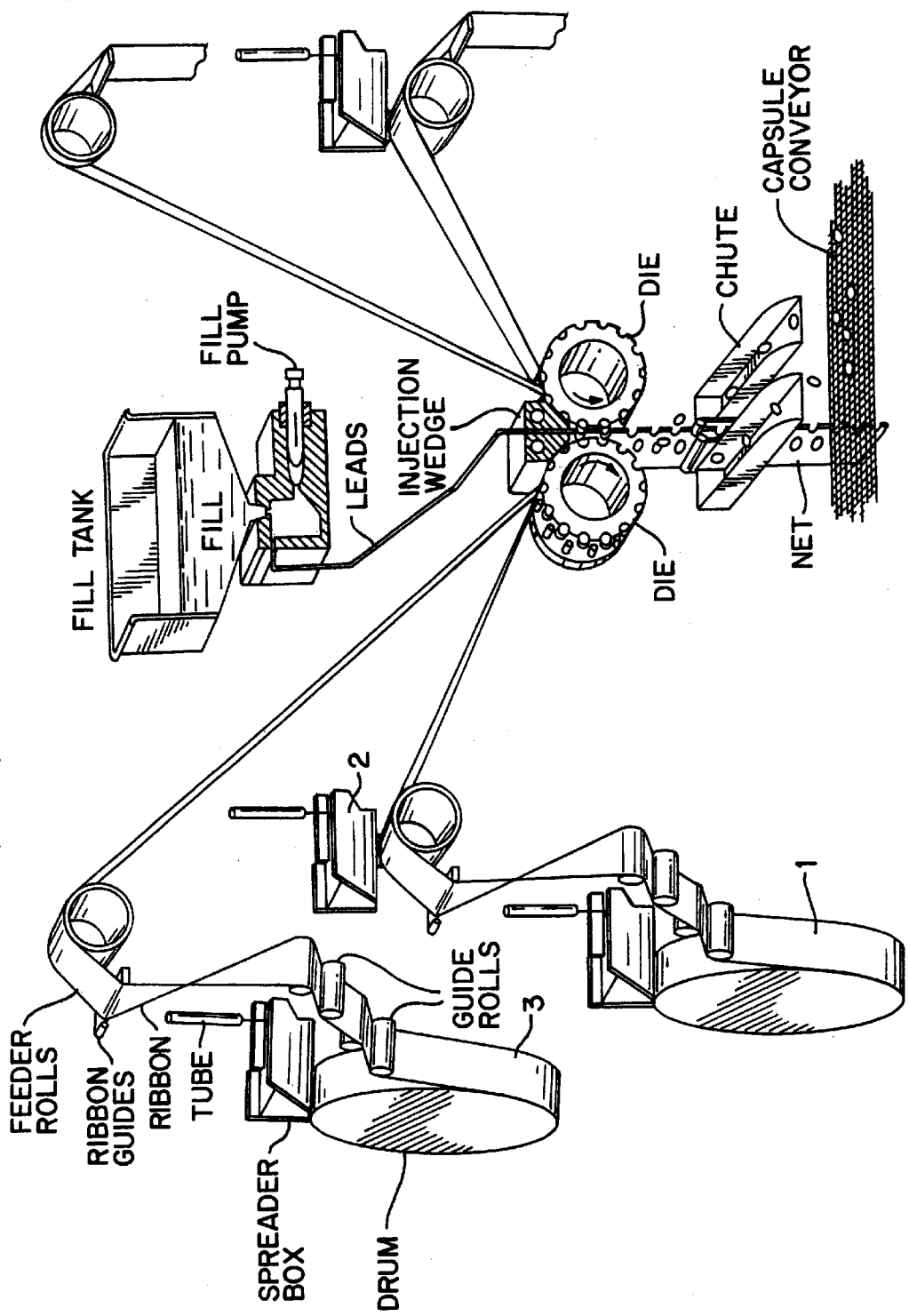
FIG. 2 is a schematic drawing of a second embodiment of the process and apparatus used in the present invention.

A suitable ribbon from silicone elastomer (thickness about 30 μm, melting point of 39° C.–40° C., pore distribution of 50 pores/mm², pore size about 50 μm) is automatically released from a third rotating drum and coupled on the internal face of the second inner layer (FIG. 1).

Capsule filling 1.43 Kg of silicone resin, having a viscosity of 300 cSt, are mixed with 1.170 Kg of nicorandil (100% assay) and the resulting viscous suspension is loaded, under pressure, in the fill tank of the fill pump of the machine for the production of the soft capsules (FIG. 1). The wet soft capsules are then dried and stabilized according to conventional method on trays, placed in drying tunnels (72 hours at 20° C.–25° C.). 18,970 soft capsules pass the visual inspection and the control tests. Yield: 72.96%.

EXAMPLE 6

Preparation of 30,500 extended release soft capsules of nicorandil 30 mg (2 oval).

Each extended release soft capsule containing

| CAPSULE FILLING | |
| --- | --- |
| nicorandil | 30.000 mg |
| silicone resin (viscosity 800 cSt) | 45.000 mg |
| white wax | 25.000 mg |
| Total weight of the content | 100.000 mg |
| CAPSULE HOUSING | |
| First outer layer | |
| gelatin | 49.246 mg |
| modified sorbitol solution 45% | 26.307 mg |
| titanium dioxide E 171 | 0.720 mg |
| iron oxide red E 172 | 0.120 mg |
| Second inner layer | |
| silicone (viscosity 150 cSt) | 6.885 mg |
| Total weight of the capsule housing | 83.278 mg |

Capsule housing/first outer layer 1,502.0 g of gelatin, 802.36 g of modified sorbitol solution 45% (in water), 21.96 g of titanium dioxide (E 171), 3.66 g of iron oxide red (E 172) and 1,055.0 g of water, are mixed. This mixture is melted, under vacuum (730–750 mm Hg) and stirring, in a stainless steel tank at a temperature between 75° C. and 80° C. until the melting is absolutely complete. The red-brown coloured gelatin mass is utilized to make the first outer layer ribbon (wet thickness of about 0.76 mm) on the fashion described before (FIG. 2).

Capsule housing/second inner layer 209.99 g of silicone, having a viscosity of about 150 cSt. are introduced in a spreader box, installed on the top of the rotating drum 1, that deposits continuously, on the internal surface of the first outer gelatin ribbon, an uniform film with a thickness of about 60 μm (FIG. 2).

Capsule filling 1.372 Kg of liquid silicone resin, having a viscosity of 800 cSt, are mixed with 915.0 g of nicorandil (100% assay). 762.5 g of white wax, previously melted at about 75° C. are added to the mixture, under stirring at 25° C. for about 5 minutes, until obtaining an uniform support. The resulting mass is loaded, under constant stirring, into the fill tank of the fill pump of the machine for the production of soft capsules. In this manner is made a delivery system that assures the extended release of the active drug substance, due to the slow liberation from the support. The wet soft capsules are then dried and stabilized according to conventional methods on trays, placed in drying tunnels (72 hours at 20° C.–25° C.). 18,950 soft capsules pass the visual inspection and the control tests. Yield: 62.13 %.

Extended release test of the soft capsules of Example 6

The test is carried out according by USP XXII, page 1581, "Extended Release Article".

The obtained results are indicated in the following table

| hours | % of nicorandil released |
| --- | --- |
| 2 h. | 25% |
| 6 h. | 42% |
| 12 h. | 70% |

EXAMPLE 7

Preparation of 25,000 extended release soft capsules of sodium bicarbonate 500 mg (20 oblong).

Each extended release soft capsule containing

| CAPSULE FILLING | |
| --- | --- |
| sodium bicarbonate | 500.0 mg |

-continued

| | |
|---|---|
| silicone resin (viscosity 600 cSt) | 470.0 mg |
| white wax | 130.0 mg |
| Total weight of the content | 1100.0 mg |
| CAPSULE HOUSING | |
| First outer layer | |
| gelatin | 261.154 mg |
| glycerol | 139.384 mg |
| titanium dioxide E 171 | 9.230 mg |
| Secand inner layer | |
| silicone (viscosity 250 cSt) | 44.984 mg |
| Total weight of the capsule housing | 454.752 mg |

Capsule housing/first outer layer 6.53 Kg of gelatin, 3.48 Kg of glycerol, 7.21 Kg of water and 0.23 Kg of titanium dioxide (E 171) are mixed thoroughly and the mixture is melted in a stainless steel tank, under vacuum and constant stirring, at a temperature between 75° C. and 80° C. When the melting is completed, the mass is used for preparing the first outer layer ribbon on the fashion already described, having a thickness of about 0.96 mm.

Capsule housing/second inner layer 1,124.0 g of silicone, having an intrinsic viscosity of about 250 cSt, are placed in a spreader box, installed on the top of the rotating drum 1, that dispenses continuously, on the internal surface of the first outer gelatin ribbon, an uniform film, having a thickness of about 75 $\mu$m (FIG. 2).

Capsule filling 11.75 Kg of silicone resin, having a viscosity of 600 cSt, are mixed with 12.5 Kg of sodium bicarbonate. 3.25 Kg of white wax, previously melted at about 75° C. are added to the mixture under stirring at 25° C. For about 5 minutes, until obtaining an uniform support. The resulting mass is loaded, under constant stirring, into the fill tank of the fill pump of the machine for the production of the soft capsules. The wet soft capsules are then dried and stabilized, according to conventional methods on trays, placed in drying tunnels (72 hours at 20° C.–25° C.). 16,825 soft capsules pass the visual inspection and the control test. Yield: 67.3%.

Extended release test of the soft capsules of Example 7

The obtained delivery system permits the extended release of the antiacid because of the slow liberation of sodium bicarbonate. The test is carried out according USP XXII, page 1581, "Extended Release Article".

The obtained results are indicated in the following table

| hours | % of NaHCO$_3$ released |
|---|---|
| 1 h. | 28% |
| 3 h. | 51% |
| 5 h. | 75% |

While the invention has been described in terms of various preferred embodiments, the skilled artisan will appreciate that various modifications, substitutions, omissions, and changes may be made without departing from the spirit thereof. Accordingly, it is intended that the scope of the present invention shall be limited solely by the scope of the following claims including equivalents thereof.

What is claimed is:

1. A unit dosage drug delivery system which comprises:
   a) a multiple layer capsule housing, comprising at least two coupled layers, sheaths or films from different materials, the first outer layer or sheath with hydrophilic character and the inner sheaths or films with hydrophobic character; and
   b) a capsule filling, embodying one or more active drug substances, with conventional or extended drug release properties, with a remarkable hydrophobic character.

2. The unit dosage drug delivery system of claim 1 wherein said multiple layer capsule housing comprises:
   a) a first outer hydrophilic layer, consisting either of a mixture of gelatin, glycerin and/or modified sorbitol solution, water or alternatively of other suitable compounds, alike polyphenyl compounds;
   b) a second inner hydrophobic film or sheath from silicone, silicone mixture or other pharmaceutically acceptable silicone polymers; and
   c) an optional inner third or additional films or sheaths, made from silicone polymers or waxes or alternatively from jaluronic acid polymers.

3. The unit dosage drug delivery system of claim 1 wherein said capsule filling, confined within the capsule housing, contains:
   a) one or more active drug substances which are admixed, dissolved, suspended or agglomerated in an hydrophobic support;
   b) silicone resin having a viscosity in the range of from 100 to 1,100 cSt and specific gravity in the range of from 0.96 to 1.02;
   c) optional components, particularly sodium laurylsarcosinate in the range from 0.1% to 2.0% and absolute ethanol in the range from 1.0% to 30.0% of the capsule filling; and
   d) optional release modifying substances providing an extended release of the active medicinal drug, said modifying substances selected from the group consisting of: beeswax, silicone waxes and natural or modified stearic acid, palmitic acid, myristic acid, lauric acid, stearyl alcohol, cetyl alcohol, glyceryl stearate, ethyl oleate, arachids oils, cotton seed oil, rape seed oil, liquid paraffin and polyethylene glycol from 400 to 20,000.

4. The unit dosage drug delivery system of claim 1 having size, shape and color of a conventional capsule for oral, rectal or vaginal administration.

5. The unit dosage drug delivery system of claim 1 wherein the capsule housing has conventional or enteric release dissolution.

6. The unit dosage drug delivery system of claim 2 wherein the first outer hydrophilic layer of the capsule housing presents a thickness at the wet state comprised between 0.50 mm and 1 mm.

7. The unit dosage drug delivery system of claim 2 wherein a second inner hydrophobic film or sheath of the capsule housing is made from silicone, having a low-medium viscosity comprised between 10 and 200,00 cSt.

8. The unit dosage drug delivery system of claim 2 wherein the second inner hydrophobic film or sheath of the capsule housing presents a thickness comprised between 0.1 and 100 $\mu$m.

9. The unit dosage drug delivery system of claim 2 having an optional inner third or multiple films or sheaths of the capsule housing, with a thickness comprised between 0.1 and 100 $\mu$m, and a melting range of about 39° C.–40° C.

10. The unit dosage drug delivery system of claim 2 having a third inner hydrophobic film or sheath of the capsule housing optionally covered with pores of suitable size, comprised between 10 and 100 $\mu$m, and a pore distribution from 2,500 to 25 pores/mm$^2$, in order to achieve a retarded diffusion of the active drug substance.

11. The unit dosage drug delivery system of claim 2 wherein the second inner hydrophobic sheath or film of the capsule housing has an intrinsic viscosity lower than that of the third inner film or sheath.

12. The unit dosage drug delivery system of claim 2 wherein the first outer hydrophilic layer represents from 83.33% to 99.96% by weight of the entire capsule housing.

13. The unit dosage drug delivery system of claim 2 wherein the sum of the second inner hydrophobic film or sheath and of the optional inner third or multiple films or sheaths, is further comprising of from 0.04% to 16.67% by weight of the entire capsule housing.

14. The unit dosage drug delivery system of claim 3 wherein the capsule filling contains one or more active drug substances, selected among the groups of oligopeptides, peptides, proteins, prostaglandins, cholesterol lowering agents, gastric antisecretories, antiacids, antiallergic agents, antiasthmatic agents, ACE inhibitors, diuretic agents, antineoplastic agents, antiviral nucleosides agents, antifungal agents, antiparkinson agents, antiepileptic agents, analgesics, non-steroidal antiinflammatories, antitussives, decongestionants, narcotics, antibiotics, cardiovasculars, their organic and inorganic salts, liophylized yeasts and vitamins.

15. The unit dosage drug delivery system of claim 3 wherein the capsule filling contains one or more pharmaceutical active drug substances in the range of from 0.0001% to 45% by weight.

16. The unit dosage drug delivery system of claim 3 wherein the release modifying substances are further comprising of from 15% to 60%, by weight of the silicone resin of the capsule filling.

17. The unit dosage drug delivery system of claim 2 wherein the multiple layer capsule housing presents an enteric release coating, obtained by conventional gastroenteric coating methods, preferably by immersion in a solution of formaldehyde dispersed in acetone in a ratio 1:60.

18. The unit dosage drug delivery system of claim 2 wherein the first outer layer of the capsule housing is made from polyphenyl compounds, and wherein the gastroenteric release coating is obtained by applying a suitable conventional coating composition.

19. The unit dosage drug delivery system of claim 14 wherein the capsule filling contains cyclosporines.

20. The unit dosage drug delivery system of claim 14 wherein the capsule filling contains omeprazole.

21. The unit dosage drug delivery system of claim 14 wherein the capsule filling contains ranitidine or its salts.

22. The unit dosage drug delivery system of claim 1 particularly suitable and convenient for delivering active drug substances, selected among the groups of oligopeptides, peptides, proteins, prostaglandins, cholesterol lowering agents, gastric antisecretories, antiacids, antiallergic agents, antiasthmatic agents, ACE inhibitors, diuretic agents, antineoplastic agents, antiviral nucleosides agents, antifungal agents, antiparkinson agents, antiepileptic agents, analgesics, non-steroidal antiinflammatories, antitussives, decongestionants, narcotics, antibiotics, cardiovasculars, their organic and inorganic salts, liophylized yeasts and vitamins, sensitive to moisture, oxidation or easily degradable from the atmosphere.

23. The unit dosage drug delivery system of claim 1 which advantageously prevents the diffusion of the water soluble active drug substances or of their pharmaceutically acceptable salts, selected among the groups of oligopeptides, peptides, proteins, prostaglandins, cholesterol lowering agents, gastric antisecretories, antiacids, antiallergic agents, antiasthmatic agents, ACE inhibitors, diuretic agents, antineoplastic agents, antiviral nucleosides agents, antifungal agents, antiparkinson agents, antiepileptic agents, analgesics, non-steroidal antiinflammatories, antitussives, decongestionants, narcotics, antibiotics, cardiovasculars, their organic and inorganic salts, liophylized yeasts and vitamins, from the capsule filling to the first outer hydrophilic layer of the capsule housing.

24. A method of preparing a unit dosage drug delivery system, which comprises the steps of:
   a) providing a capsule housing comprising the following ingredients:
      i) a first outer hydrophilic layer, consisting either of a mixture or gelatin, glycerin and/or modified sorbitol solution, water or alternatively of other suitable compounds, alike polyphenyl compounds;
      ii) a second inner hydrophobic film or sheath from silicone, silicone mixture or other pharmaceutically acceptable silicone polymers; and
      iii) an optional inner third or additional films or sheaths, made from silicone polymers or waxes or alternatively from jaluronic acid polymers; and
   b) providing a capsule filling comprising the following ingredients:
      i) one or more active drug substances which are admixed, dissolved, suspended or agglomerated in an hydrophobic support;
      ii) silicone resin having a viscosity in the range of from 100 to 1,100 cSt and specific gravity in the range of from 0.96 to 1.02;
      iii) optional components particularly sodium laurylsarcosinate in the range from 0.1% to 2.0% and absolute ethanol in the range from 1.0% to 30.0% of the capsule filling; and
      iv) optional release modifying substances providing an extended release of the active medicinal drug, said modifying substances selected from the group consisting of: beeswax, silicone waxes and natural or modified stearic acid, palmitic acid, myristic acid, lauric acid, stearyl alcohol, cetyl alcohol, glyceryl stearate, ethyl oleate, arachids oil, cotton seed oil, rape seed oil, liquid paraffin and polyethylene glycol from 400 to 20,000.

25. The method of claim 24 wherein the capsule housing has conventional or enteric release dissolution.

26. The method of claim 24 wherein the first outer hydrophilic layer of the capsule housing presents a thickness at the wet state comprised between 0.50 mm and 1 mm.

27. The method of claim 24 wherein a second hydrophobic inner film or sheath of the capsule housing is made from silicone, having a low-medium viscosity comprised between 10 and 200,000 cSt.

28. The method of claim 24 wherein the second inner hydrophobic film or sheath of the capsule housing presents a thickness comprised between 0.1 and 100 $\mu$m.

29. The method of claim 24 having an optional inner third or multiple films or sheaths of the capsule housing, with a thickness comprised between 0.1 and 100 $\mu$m and a melting range of about 39° C.–40° C.

30. The method of claim 24 wherein the third film or sheath of the capsule housing is optionally covered with pores of suitable size, comprised between 10 and 100 $\mu$m, and a pore distribution from 2,500 to 25 pores/mm$^2$, in order to achieve a retarded diffusion of the drug substance.

31. The method of claim 24 wherein the second inner hydrophobic sheath or film of the capsule housing has an intrinsic viscosity lower than that of the optional third inner film or sheath.

32. The method of claim 24 wherein the first hydrophilic outer layer represents from 83.33% to 99.69% by weight of the entire capsule housing.

33. The method of claim 24 wherein the sum of the second inner hydrophobic film or sheath and of the optional inner third or multiple film or sheath, is further comprising from 0.04% to 16.67% by weight of the entire capsule housing.

34. The method of claim 24 wherein the capsule filling contains one or more active drug substances, selected among the groups of oligopeptides, peptides, proteins, prostaglandins, cholesterol lowering agents, gastric antisecretories, antiacids, antiallergic agents, antiasthmatic agents, ACE inhibitors, diuretic agents, antineoplastic agents, antiviral nucleosides agents, antifungal agents, antiparkinson agents, antiepileptic agents, analgesics, non-steroidal antiinflammatories, antitussives, decongestionants, narcotics, antibiotics, cardiovasculars, their organic and inorganic salts, liophylized yeasts and vitamins.

35. The method of claim 24 wherein the capsule filling contains one or more pharmaceutical drug substances, in the range of from 0.0001% to 45% by weight.

36. The method of claim 24 wherein the capsule filling contains the release modifying substances further comprising of from 15% to 60% by weight of the silicon resin, excluding the active drug substance.

37. The method of claim 24 wherein the multiple layer capsule housing presents an enteric release coating, obtained by conventional gastroenteric coating methods, preferably by immersion in a solution of formaldehyde dispersed in acetone in a ratio 1:60.

38. The method of claim 24 wherein the first outer layer of the capsule housing is made from polyphenyl compounds, wherein the gastroenteric release coating is obtained by applying a suitable conventional coating composition.

39. A medicated composition which comprises a pharmaceutically acceptable carrier and a therapeutically effective amount of a unit dosage drug delivery system comprising:
   a) a first outer hydrophilic layer, consisting either of a mixture or gelatin, glycerin and/or modified sorbitol solution, water or alternatively or other suitable compounds, alike polyphenyl compounds;
   b) a second inner hydrophobic film or sheath from silicone, silicone mixture or other pharmaceutically acceptable silicone polymers;
   c) an optional inner third or additional films or sheaths, made from silicone polymers or waxes or alternatively from jaluronic acid polymers; and
   d) a capsule filling comprising:
      i) one or more active drug substances which are admixed, dissolved, suspended or agglomerated in an hydrophobic support;
      ii) silicone resin having a viscosity in the range of from 100 to 1,100 cSt and specific gravity in the range of from 0.96 to 1.02;
      iii) optional components particularly sodium laurylsarcosinate in the range from 0.1% to 2.0% and absolute ethanol in the range from 1.0% to 30.0% of the capsule filling; and
      iv) optional release modifying substances, providing an extended release of the active medicinal drug, said modifying substances selected from the group consisting of: beeswax, silicone waxes and natural or modified stearic acid, palmitic acid, myristic acid, lauric acid, stearyl alcohol, cetyl alcohol, glyceryl stearate, ethyl oleate, arachids oil, cotton seed oil, rape seed oil, liquid paraffin and polyethylene glycol from 400 to 20,000.

40. The medicated composition of claim 39 adapted for oral, rectal or vaginal administration.

41. The medicated composition of claim 39 wherein the active drug substances are advantageously protected from atmosphere, from oxidation, and from moisture-induced hydrolytic or degradation processes.

42. The medicated composition of claim 39 wherein the total moisture of the capsule filling is less the 1.

43. The medicated composition of claim 39 wherein the active drug substance is conveniently protected from moisture, oxidation and atmospheric degradation processes.

44. The medicated composition of claim 39 wherein the diffusion of the active drug substance, from the capsule filling to the hydrophilic first outer layer of the capsule housing, is advantageously prevented by the hydrophobic second inner layer.

45. The medicated composition of claim 39 wherein the possible unpleasant taste or odor of the active drug substance is suitably masked, improving the administration compliance.

46. The medicated composition of claim 39 adapted to extend the delivery of the active drug substance thereof, as to maintain a therapeutically plasma level thereof for a desired interval.

47. The medicated composition of claim 39 for eliciting a therapeutic response in a mammalian organism in need of such treatment, comprising administering to such organism a therapeutically effective amount of the unit dosage drug delivery system.

48. A pharmaceutical product in unit dosage form which comprises:
   a) a multiple layer capsule housing having two or more layers, said layers being of different materials, wherein the outer layer possesses a hydrophilic character and the inner layer possesses a hydrophobic character; and
   b) a filling comprising one or more drug substances which are admixed, dissolved, suspended or agglomerated in an hydrophobic support.

* * * * *

UNITED STATES PATENT AND TRADEMARK OFFICE
CERTIFICATE OF CORRECTION

PATENT NO. : 5,814,338
DATED : September 29, 1998
INVENTOR(S) : Paolo A. Veronesi It is certified that error appears in the above-indentified patent and that said Letters Patent is hereby corrected as shown below:

<u>In the Claims</u>

In Claim 7, line 4, replace "200,00" with --200,000--.

In Claim 39, line 5, replace the first occurrence of "or" with ----of--.

Signed and Sealed this

Thirteenth Day of April, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,814,338
DATED : September 29, 1998
INVENTOR(S) : Paolo A. Veronesi It is certified that error appears in the above-identified patent and that said Letters Patent is hereby corrected as shown below:

In claim 7, line 4, please change "200,00" to --200,000--.

In claim 42, line 2, please change "less the" to --less than--.

Signed and Sealed this

Twenty-seventh Day of March, 2001

Attest:

NICHOLAS P. GODICI

*Attesting Officer*     *Acting Director of the United States Patent and Trademark Office*